United States Patent [19]

Brooks et al.

[11] Patent Number: 5,169,854
[45] Date of Patent: Dec. 8, 1992

[54] N-SUBSTITUTED-FURYLALKENYL HYDROXAMIC ACID AND N-HYDROXYUREA COMPOUNDS HAVING LIPOXYGENASE INHIBITORY ACTIVITY

[75] Inventors: Dee W. Brooks, Libertyville; Andrew O. Stewart, Wildwood; Pramila Bhatia, Mundelein, all of Ill.; Richard A. Craig, Racine, Wis.

[73] Assignee: Abbott Laboratories, Abbott Park, Ill.

[21] Appl. No.: 841,968

[22] Filed: Feb. 26, 1992

[51] Int. Cl.⁵ .................. C07D 405/02; C07D 307/40; A61K 31/47; A61K 31/34; A61K 31/44
[52] U.S. Cl. ...................................... 514/314; 514/461; 514/327; 514/336; 546/178; 546/283; 549/479
[58] Field of Search ............... 549/479; 546/178, 283; 514/314, 461, 336

[56] References Cited

U.S. PATENT DOCUMENTS

| | | | |
|---|---|---|---|
| 4,097,487 | 6/1978 | Murakami et al. | 549/479 |
| 4,738,986 | 4/1988 | Kneen et al. | 514/574 |
| 4,769,461 | 9/1988 | Musser et al. | 546/179 X |

FOREIGN PATENT DOCUMENTS 0292699 11/1988 European Pat. Off. .
0299761 1/1989 European Pat. Off. .

Primary Examiner—David B. Springer
Attorney, Agent, or Firm—Jerry F. Janssen

[57] ABSTRACT

Compounds useful in inhibiting the biosynthesis of leukotrienes have the structure

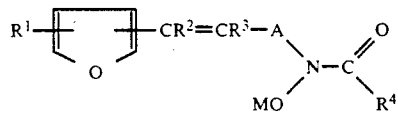

where M is hydrogen, a pharmaceutically acceptable cation, or a metabolically cleavable group, $R^4$ is alkyl, cycloalkyl or $-NR^5R^6$, where $R^5$ and $R^6$ are hydrogen, alkyl, cycloalkyl or alkanoyl, where A is a valence bond or is a straight or branched divalent alkylene group of from one to twelve carbon atoms, $R^2$ and $R^3$ are independently selected from hydrogen, straight or branched alkyl of from one to twelve carbon atoms, halogen, or trifluoroalkyl, and $R^1$ is selected from phenoxy, phenylthio, 2-, 3-, or 4-pyridyloxy, 1 or 2-naphthyloxy, or 2,4,5, or 8-quinolyloxy, all optionally substituted with alkyl, haloalkyl, alkoxy, hydroxy or halogen.

8 Claims, No Drawings

N-SUBSTITUTED-FURYLALKENYL HYDROXAMIC ACID AND N-HYDROXYUREA COMPOUNDS HAVING LIPOXYGENASE INHIBITORY ACTIVITY

TECHNICAL FIELD

This invention relates to compounds having activity to inhibit lipoxygenase enzymes, to pharmaceutical compositions comprising these compounds, and to a medical method of treatment. More particularly, this invention concerns certain substituted furanylalkenylene ureas and hydroxamic acids which inhibit leukotriene biosynthesis, to pharmaceutical compositions comprising these compounds and a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardinal injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 0 292 699 to Summers discloses and claims certain N-hydroxy-N-[(substituted thienyl)alkyl]urea compounds useful as antiinflammatory and antiallergic agents.

European Patent Application 0 299 761 to Salmon, et al. discloses and claims certain (substituted phenoxy)-phenylalkenyl hydroxamic acids and their salts which are useful as agents for inhibiting lipoxygenase and cyclooxygenase activity.

SUMMARY OF THE INVENTION

In its principal embodiment, the present invention provides certain substituted alkenylene compounds which inhibit lipoxygenase enzyme activity and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure

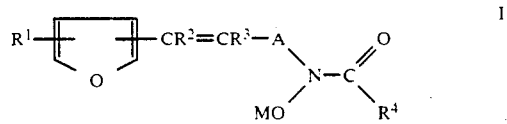

and the pharmaceutically acceptable salts thereof wherein A is a valence bond or is a straight or branched divalent alkylene group of from one to twelve carbon atoms. The group M represents hydrogen, a pharmaceutically acceptable cation, or a pharmaceutically acceptable metabolically cleavable group.

The group $R^1$ is selected from the group consisting of a) phenoxy, optionally substituted with alkyl of from one to six carbon atoms, haloalkyl of from one to six carbon atoms, alkoxy of from one to six carbon atoms, hydroxy or halogen; b) phenylthio, optionally substituted with alkyl of from one to six carbon atoms, haloalkyl of from one to six carbon atoms, alkoxy of from one to six carbon atoms, hydroxy or halogen; c) 2-, 3-, or 4-pyridyloxy, optionally substituted with alkyl of from one to six carbon atoms, haloalkyl of from one to six carbon atoms, alkoxy of from one to six carbon atoms, hydroxy or halogen; d) 2-, 3-, or 4-pyridylmethoxy, optionally substituted with alkyl of from one to six carbon atoms, haloalkyl of from one to six carbon atoms, alkoxy of from one to six carbon atoms, hydroxy or halogen; e) 1, or 2-naphthyloxy, optionally substituted with alkyl of from one to six carbon atoms, haloalkyl of from one to six carbon atoms, alkoxy of from one to six carbon atoms, hydroxy or halogen; f) 2-, 4-, 5-, or 8-quinolyloxy, optionally substituted with alkyl of from one to six carbon atoms, haloalkyl of from one to six carbons atoms, alkoxy of from one to six carbon atoms, hydroxy or halogen; and g) 2-, 4-, 5-, or 8-quinolylmethoxy, optionally substituted with alkyl of from one to six carbon atoms, haloalkyl of from one to six carbon atoms, alkoxy of from one to six carbon atoms, hydroxy or halogen.

The groups $R^2$ and $R^3$ are independently selected from the group consisting of hydrogen, straight or branched alkyl of from one to twelve carbon atoms, halogen, or trifluoroalkyl.

$R^4$ is selected from the group consisting of hydrogen, alkyl of from one to twelve carbon atoms, cycloalkyl of from three to eight carbon atoms, and $-NR^5R^6$ where $R^5$ is selected from the group consisting of hydrogen, alkyl of from one to six carbon atoms, hydroxyalkyl of from one to six carbon atoms, and alkoxyalkyl in which the alkoxy portion and the alkyl portion each contain, independently, from one to six carbon atoms. $R^6$ is selected from the group consisting of hydrogen, alkyl of from one to six carbon atoms, hydroxyalkyl of from one to six carbon atoms, alkoxyalkyl in which the alkoxy portion and the alkyl portion each contain, independently, from one to six carbon atoms, alkanoyl of from two to eight carbon atoms, carbocyclic aryl, and (carbocyclic aryl)alkyl in which the alkyl portion contains from one to six carbon atoms.

In another embodiment, the present invention provides pharmaceutical compositions for inhibiting leukotriene biosynthesis which comprise a therapeutically effective amount of compound as defined above in combination with a pharmaceutically acceptable carrier.

In a still further embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION DEFINITIONS OF TERMS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

"Alkylamino" and "dialkylamino" refer, respectively, to one or two alkyl groups, as defined above, attached to the parent molecular moiety through a nitrogen atom and are represented by methyl amino, dimethylamino, ethyl- and diethylamino, methylethylamino, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyopentyl, cyclohexyl, bicyclo[2.2.1]heptanyl, and bicyclo[2.2.2]octanyl.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkanoyl" represents an alkyl group, as defined above, attached to the parent molecular moiety through a carbonyl group. Alkanoyl groups are exemplified by acetyl, propionyl, butanoyl and the like.

The term "carbocyclic aryl" denotes a monovalent aromatic carbocyclic ring group derived by the removal of a single hydrogen atom from a monocyclic or bicyclic fused or non-fused ring system obeying the "$4n+2\pi$ electron" or Huckel aromaticity rule. Examples of carbocyclic aryl groups include phenyl, 1- and 2-naphthyl, biphenyl, and the like.

The term "(carbocyclic aryl)alkyl" refers to a carbocyclic aryl group, as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "metabolically cleavable group" denotes a group which is cleaved in vivo to yield the parent molecule of the structural formulae indicated above wherein M is hydrogen. Examples of metabolically cleavable groups include $-COR$, $-COOR$, $-CONRR$ and $-CH_2OR$ radicals where R is selected independently at each occurrence from alkyl, trialkylsilyl, carbocyclic aryl or carbocyclic aryl substituted with one or more of $C_1-C_4$ alkyl, halogen, hydroxy or $C_1-C_4$ alkoxy. Specific examples of representative metabolically cleavable groups include acetyl, methoxycarbonyl, benzoyl, methoxymethyl and trimethylsilyl groups.

PREFERRED EMBODIMENTS

Although the configuration of groups about the carbon-carbon double bond is not specified in the generic structural formula I above, the preferred configuration is the E ("entgegen") or trans-configuration.

One preferred aspect of the compound embodiment of the invention provides compounds which comprise a class of hydroxamic acids and their salts where $R^4$ is alkyl of from one to twelve carbon atoms or cycloalkyl of from three to eight carbon atoms and M is hydrogen or a pharmaceutically acceptable cation.

A particularly preferred aspect of the compound embodiment of the invention provides compounds which comprise a class of N-hydroxy-N-[(substituted furyl)-alkenyl]ureas and their salts where M is hydrogen or a pharmaceutically acceptable salt and $R^4$ is $-NR^5R^6$ where $R^5$ and $R^6$ are as defined above. Most preferred compounds are those in which M is hydrogen; $R^1$ is phenoxy, optionally substituted with alkyl of from one to six carbon atoms, haloalkyl of from one to six carbon atoms, alkoxy of from one to six carbon atoms, hydroxy or halogen; and $R^4$ is amino, alkylamino or dialkylamino.

Representative examples of compounds falling within the scope of the present invention include, but are not limited to:

E-N-[4-(5-(4-fluorophenoxy)-2-furanyl)but-3-en-2-yl]-
   N-hydroxyurea;

E-N-[3-(5-phenoxy-2-furanyl)-2-propenyl]-N-hydroxyurea;

Z-N-[4-(5-(4-fluorophenoxy)-2-furanyl)-2-fluorobut-3-en-2-yl]-N-hydroxyurea;

E-N-[4-(5-phenoxy-2-furanyl)but-3en-2-yl]-N-hydroxyurea;

E-N-[4-(5-(2-fluorophenoxy)-2-furanyl)but-3-en-2-yl]-N-hydroxyurea;

E-N-[4-(5-(2,4-difluorophenoxy)-2-furanyl)but-3-en-2-yl]-N-hydroxyurea;

E-N-[4-(5-(2-methyl-4-fluorophenoxy)-2-furanyl)but-3-en-2-yl]-N-hydroxyurea;

E-N-[4-(5-(4-chlorophenoxy)-2-furanyl)but-3-en-2-yl]-N-hydroxyurea;

E-N-[4-(5-(4-bromophenoxy)-2-furanyl)but-3-en-2-yl]-N-hyroxyurea;

E-N-[4-(5-(4-n-butoxyphenoxy)-2-furanyl)but-3-en-2-yl]-N-hydroxyurea;

E-N-[4-(5-(4-n-butylphenoxy)-2-furanyl)but-3-en-2-yl]-N-hydroxyurea;

E-N-[4-(5-(4-thiomethylphenoxy)-2-furanyl)but-3-en-2-yl]-N-hydroxyurea;

E-N-[4-(5-(4-cyanophenoxy)-2-furanyl)but-3-en-2-yl]-N-hydroxyurea;

E-N-[4-(5-(4-fluorophenoxy)-3-methyl-2-furanyl)but-3-en-2-yl]-N-hydroxyurea;

E-N-[4-(5-(2-naphthoxy)-2-furanyl)but-3-en-2-yl]-N-hydroxyurea;

E-N-[4-(5-quinolyloxy-2-furanyl)but-3-en-2-yl]-N-hydroxyurea;

E-N-[4-(5-(4-fluorothiophenoxy)-2-furanyl)but-3-en-2-yl]-N-hydroxyurea;

E-N-[4-(5-(4-thiophenoxy)-2-furanyl)but-3-en-2-yl]-N-hydroxyurea;

E-N-[4-(5-(3-pyridnyloxy)but-3-ene-2-yl]-N-hydroxyurea;

E-N-[4-(5-(6-methyl-3-pyridnyloxy)-2-furanyl)but-3-en-2-yl]-N-hydroxyurea;

E-N-[4-(5-(5-chloro-3-pyridnyloxy)-2-furanyl)but-3-en-2-yl]-N-hydroxyurea;

E-N-[4-(5-(2-mercaptopyridinyl)-2-furanyl)but-3-en-2-yl]-N-hydroxyurea;

E-N-[4-(5-(4-fluorophenoxy)-2-furanyl)but-3-en-2-yl]-N-hydroxyacetamide;

E-N-[3-(5-phenoxy-2-furanyl)-2-propenyl]-N-hydroxyacetamide;

E-N-[4-(5-(2,4-difluorophenoxy)-2-furanyl)but-3-en-2-yl]-N-hydroxyacetamide;

E-N-[4-(5-(4-n-butoxyphenoxy)-2-furanyl)but-3-en-2-yl]-N-hydroxyacetamide;

E-N-[4-(5-(4-fluorothiophenoxy)-2-furanyl)but-3-en-2-yl]-N-hydroxyacetamide;

E-N-[4-(5-(3-pyridnyloxy)-2-furanyl)but-3-en-2-yl]-N-hydroxyacetamide;

and compounds having the names above wherein the N-hydroxy hydrogen atom is replaced by a pharmaceutically acceptable cation, or a pharmaceutically acceptable metabolically cleavable group.

Certain compounds of this invention may exist in stereoisomeric forms by virtue of the presence of one or more chiral centers. The present invention contemplates all such stereoisomers, including R- and S-enantiomers, diastereomers, and mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the pure desired enantiomers. Alternatively, where the molecule contains a basic functional group such as amino or an acidic functional group such as carboxyl diastereomeric salts are formed with an appropriate optically active acid or base, followed by resolution of the diastereomers thus formed by fractional crystallization or chromatographic means well known in the art and subsequent recovery of the pure enantiomers.

Certain compounds of the present invention may contain a basic functional group such as amino, alkylamino, or dialkylamino and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts, "*J. Pharm. Sci.*, 66: 1–19 (1977) which is incorporated herein by reference.)

In other cases, the compounds may contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate or bicarbonate of a pharmaceutically acceptable metal cation or with ammonia, or an organic primary, secondary, or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine, and the like. (See, for example S. M. Berge, et al., "Pharmaceutical Salts, "*J. Pharm. Sci.*, 66: 1–19 (1977) which is incorporated herein by reference.)

LIPOXYGENASE INHIBITION

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 $\mu$M) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit 5-lipoxygenase enzyme activity as illustrated by data presented for representative examples presented in Table 1.

TABLE 1

| 5-Lipoxygenase Inhibitory Activity of Representative Compounds of the Present Invention | |
|---|---|
| Example | $IC_{50} (10^{-6} M)$ |
| 1 | 0.16 |
| 2 | 83% at 0.20 |
| 3 | 77% at 0.39 |

INHIBITION OF LEUKOTRIENE BIOSYNTHESIS

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W. *Fed. Proc., Fed. Am. Soc. Exp. Biol.* 1985 (44), 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results for representative examples of the present invention are presented in Table 2.

TABLE 2

| Leukotriene Biosynthesis Inhibitory Activity of Representative Compounds of the Present Invention | |
|---|---|
| Example | Percent Inhibition of Leukotriene Biosynthesis at an Oral Dose of 100 μmol/kg |
| 1 | 98 |
| 2 | 99 |

PREPARATION OF COMPOUNDS OF THIS INVENTION

Compounds of this invention can be prepared as illustrated in Reaction Scheme 1. The carbonyl intermediate, II, is subjected to a Wittig-Horner-Emmons type olefination reaction or malonic acid condensation to provide the corresponding olefinic intermediate containing a carbonyl group which can be further converted to the hydroxylamine intermediate, III, by known methods (such as oxime formation and reduction or reduction of the carbonyl to an alcohol and activation of this followed by substitution with a suitable hydroxylamine derivative to provide the hydroxylamine intermediate). This intermediate, III, is converted to the desired hydroxamic acid compounds, Ia, by treatment with the corresponding acylhalide (RCOX) and base to provide the intermediate N-O-diacylhydroxylamine which is subsequently treated with hydroxide to selectively cleave the O-acyl group to give the desired compound, Ia. Alternatively, intermediate, III, is converted to the desired N-hydroxyureas, Ib, by known methods using the appropriate isocyanate such as trimethylsilyl isocyanate, HN=C=O, or alkyl, cycloalkyl, or carbocyclic aryl isocyanates.

Reaction Scheme 1

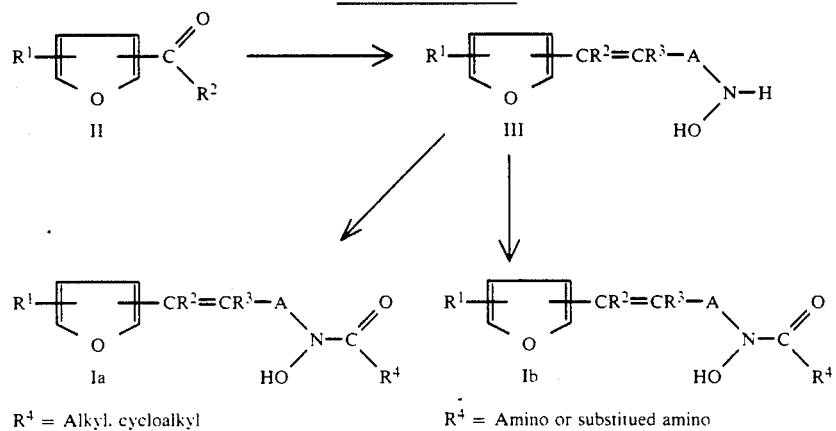

$R^4$ = Alkyl, cycloalkyl $R^4$ = Amino or substitued amino

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example. Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

EXAMPLE 1

Preparation of E-N-[4-(5-(4-Fluorophenoxy)-2-furanyl)but-3-en-2-yl]-N-hydroxyurea

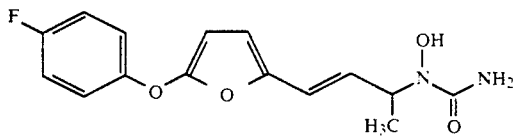

Step a): 5-(4-fluorophenoxy)-2-furfuraldehyde

To a stirred suspension of pentane washed 80% sodium hydride (5.3 g, 177 mmol) in THF (200 mL) under argon was added p-fluorophenol (19.9 g, 177 mmol) in small portions as a solid. After gas evolution had ended the THF suspension was stired an additional 0.5 h. To this cooled (0° C.) stirred mixture was added 5-nitro furfuraldehyde (25 g, 177 mmol) as a THF(50 mL) solution via dropping funnel. After the addition the reaction mixture was stirred 2 hours and a small amount of water was cautiously added. The mixture was concentrated and the residue dissolved in ether and filtered through celite. The filtrate was washed with 10% aqueous NaOH (3×100 mL), water (3×100 mL) and dried(MgSO$_4$). The mixture was concentrated and the resulting solid was dissolved in ethyl acetate, treated with decolorizing carbon, filtered and concentrated. The solid obtained was recrystalized from ether/hexane to afford 25 g (68%) of desired aldehyde as a slightly yellow solid.

Step b): 1-[3-(4-fluorophenoxy)-2-furyl]butene-3-one

To a stirred suspension of the aldehyde (5 g, 24.3 mmole) obtained above and potassium carbonate (6.72 g, 48.6 mmole) in THF was added dimethyl(2-oxopropyl)phosphonate (4.03 g, 24.3 mmole). The mixture was heated to reflux and stirred for 17 hours. The mixture was cooled, filtered and the solids washed with additional ether. The combined filtrates were concentrated and purified by column chromatography (SiO$_2$). The column was eluted with 33% ether/hexanes to afford 4.9 g of the desired unsaturated ketone as a yellow oil.

Step c): [4-(5-(4-fluorophenoxy)-2-furyl)-4-but-3-en-2-yl] hydroxylamine

To a stirred 1:1 ethanol/pyridine solution (40 mL) of the ketone (4.9 g, 20.3 mmole) obtained above was added hydroxylamine hydrochloride (5.0 g, 72.5 mmole). The mixture was stirred for one hour at room temperature and concentrated. The residue was partitioned between ether (300 mL) and 2N aqueous HCl (150 mL). The ether layer was washed with additional 2N HCl solution (150 mL, 2×), H$_2$O, brine and dried (MgSO$_4$) to afford 5.5 g of a mixture of oximes as a thick yellow oil, that was used without further purification. The oximes obtained in this manner (5.5 g, 21.1 mmol) were dissolved in 1:1 THF/acetic acid (50 mL). To this stirred solution was added sodium cyanoborohydride (2.0 g, 31.6 mmole) in several small portions. The mixture was stirred for 2 hours at ambient temperature and an additional portion of sodium cyanoborohydride was added and the mixture stirred for 2 hours more. The mixture was concentrated and the residue dissolved in ethyl acetate. The ethyl acetate solution was washed with saturated aqueous sodium bicarbonate, water, brine and dried (MgSO$_4$). The crude hydroxylamine was used without further purification.

Step d): E-N-[4-(5-(4-fluorophenoxy)-2-furanyl)but-3-en-2-yl]-N-hydroxyurea

The hydroxylamine obtained above was dissolved in THF (50 mL). To this stirred solution was added trimethylsilylisocyanate (3.64 g, 31.6 mmole). The reaction mixture was stirred for 2 hours at room temperature and concentrated. The residue was purified by column chromatography (SiO2); eluting with 5% MeOH/CH$_2$Cl$_2$ affored 1.5 g of an off white solid. Recrystalization from ethyl acetate/hexanes affored the title compound as a white solid. m.p.: 97°–99° C. (dec). $^1$H NMR (300 MHz, DMSO-d6)$\delta$ TMS: 1.17 (d, J=7 Hz, 3H), 4.75 (m, 1H), 5.72 (d, J=3 Hz, 1H), 5.59 (dd, J=16.5, 6 Hz, 1H), 6.24 (d, J=16.5 Hz, 1H), 6.35 (m, 3H), 7.12–7.31 (m, 4H), 9.03 (s, 1H). MS(DCI-NH$_3$) m/e, 324 (M+NH$_4$)$^+$, 307 (M+1)$^+$, 231.

EXAMPLE 2

Preparation of N-hydroxy-N-[3-(5-phenoxyfur-2-yl)prop-2-enyl]urea

Step a): Preparation of 3-(5-phenoxy-2-furyl)acrylic acid

To a stirred solution of (5-phenoxy)furan-2-carboxaldehyde (17.0 g, 90.4 mmol) in pyridine (75 mL) was added malonic acid (18.8 g, 181 mmol) and morpholine (0.5 mL). The mixture was heated to reflux and stirred for 17 hours. The mixture was cooled and poured into 10% aqueous HCl/ice. The tan solid was collected, washed and dried to give the desired acid which was used without further purification.

Step b): Preparation of N,O,dimethyl-3-(5-phenoxyfur-2-yl)acrylamide

The acid (6.35 g, 27.61 mmol) obtained above was dissolved in dry methylene chloride (100 mL). To this stirred solution was added oxalyl chloride (5.27 g, 41.1 mmol) and DMF (~1 mL). The mixture was stirred for 3 hours and concentrated to dryness. The residue was dissolved in fresh dry methylene chloride (100 mL) and to this stirred solution was added pyridine (7 g, 83 mmol) and N,O-dimethylhydroxylamine hydrochloride (4 g, 41.4 mmol). The reaction was stirred for 2 hours and concentrated. The resulting reside was partitioned between water and ethyl acetate. The aqueous layer was washed with ethyl acetate and the organic layers combined, dried (MgSO$_4$) and concentrated. The residue was purified by flash column chromotography (SiO2, eluted with 1:1 hexanes/ethylacetate) to afford 7.1 g (94%) of the unsaturated amide as an off white solid.

Step c): Preparation of 3-(5-phenoxyfur-2-yl)acrolein

The unsaturated amide obtained above was treated with 1.5 equivalents of DIBAL in methylene chloride at −78° C. The reaction was poured into 10% aqueous HCl and extractive work up gave crude aldehyde that was used without further purification. The crude aldehyde obtained in this manner was converted to the title compound by the method described for example 1 to afford a white crystaline solid. mp: 125.5°–128° C.; NMR (300 MHz, DMSO-d$_6$) δ4.03 (3H, d, J=6 Hz), 5.28 (1H, d, J=3 Hz), 5.89 (1H, m), 6.28–6.37 (3H, m), 6.40 (1H, d, J=3 Hz), 7.10 (2H, m), 7.20 (1H, m), 7.43 (2H, m), 9.32 (1H, s); MS m/e (DCI/NH$_3$) 275 (M+H)$^+$; 199.

EXAMPLE 3

Preparation of Z-N-[4-(5-(4-fluorophenoxy)-2-furanyl)-2-fluorobut-3-en-2-yl]-N-hydroxyurea Step a): Z-[4-(5-(4-Fluorophenoxy)-2-furanyl)-2-fluorobut-3-enoic acid, ethyl ester To a stirred THF(20 mL) solution of NaH 0.7 g (23.3 mmol) at 0° C. was added 5.64 g (23.3 mmol) diethyl ethyl fluoroacetophosphonate. The reaction was stirred for 15 min. To this stirred mixture was added 5-(4-fluorophenoxy)-2-furfural 4.00 g (19.4 mmol) as a THF (3 mL) solution. The reaction was then stirred for 1 h and concentrated. Purification by chromatography (silica/gel, eluting with ether/hexanes as eluent) gave 3.4 g of the E olefin (60%) (Rf=0.69 in 20% ethylacetate/hexanes) as an oil and 1.2 g of the Z olefin (21%) (Rf=0.58 in 20% ethylacetate/hexanes) as an oil: MS (DCI/NH$_3$) m/e 312 (M=NH$_4$)$^-$, 295 (M+H)$^+$. Z isomer $^1$H NMR (300 MHz) (CDCl$_3$) δ1.35 (t, J=6.8 Hz, 3H), 4.31 (q, J=6.8, 2H), 5.56 (d, J=3.4 Hz, 1H), 6.81 (d, J=33.5 Hz, 1H), 6.81 (d, J=3.4 Hz, 1H), 7.03–7.26 (m, 4H)

Step b): Z-[4-(5-(4-fluorophenoxy)-2-furanyl)-2-fluorobut-3-enoic acid

To stirred solution of of Z-[4-(5-(4-fluorophenoxy)-2-furanyl)-2-fluoro-but-3-enoic acid, ethyl ester (2.59 g, 8.81 mmol) in 10 ml isopropyl alcohol was added 15.4 ml of a 2M LiOH (30.8 mmol) under N$_2$ at 25° C. After 1 hr. the reaction was poured into cold 1N H$_3$PO$_4$ and thoroughly extracted with ethylacetate. The organic layers were combined, washed once with brine, dried over MgSO$_4$ and evaporated to yield 2.20 g (100%) of the desired acid: MS (DCI/NH$_3$) m/e 284 (M=NH$_4$)$^+$, 267 (M+H)$^+$; $^1$H NMR (300 MHz) (CDCl$_3$) 5.58 (d, J=3.75 Hz, 1H), 6.94 (d, J=32.25 Hz, 1H), 6.90 (d, J=3.75 Hz, 1H), 7.05–7.13 (m, 4H). The title compound was prepared as described for example 2, substituting the acid prepared above for 3-[5-phenoxyfur-2-yl]acrylic acid in part b. m.p.: 164°–165° C. (dec) MS (DCI/NH$_3$) m/e 342 (M=NH$_4$)$^+$, 325 (M+H)$^+$, 325 (M+H)$^+$; 1H NMR (300 MHz) (DMSO-d6) 1.24 (d, J=7.5 Hz, 3H), 4.97 (m, 1H), 5.78 (d, J=39.0 Hz, 1H), 5.81 (d, J=3.0 Hz, 1H), 6.43 (s, 1H), 6.48 (d, J=3.0 Hz, 1H), 7.12–7.28 (m, 4H), 9.24 (s, 1H).

The compounds represented in Table 3 can be prepared according to the method described in Example 1, except substituting the appropriate alcohol or thiol for p-fluorophenol.

TABLE 3

| Example | Product |
|---------|---------|
| 4 | 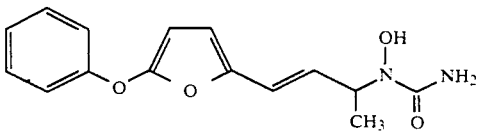<br>E-N-[4-(5-phenoxy-2-furanyl)but-3-en-2-yl]-N-hydroxyurea |
| 5 | 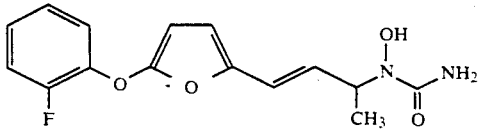<br>E-N-[4-(5-(2-fluorophenoxy)-2-furanyl)but-3-en-2-yl]-N-hydroxyurea |
| 6 | 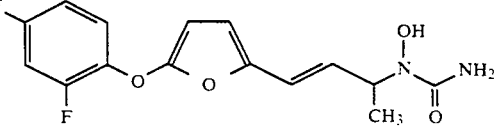<br>E-N-[4-(5-(2,4-difluorophenoxy)-2-furanyl)but-3-en-2-yl]-N-hydroxyurea |

TABLE 3-continued

| Example | Product |
|---|---|
| 7 | 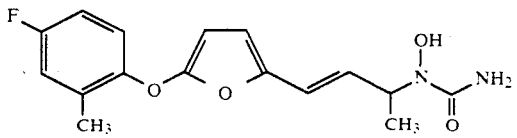<br>E-N-[4-(5-(2-methyl-4-fluorophenoxy)-2-furanyl)but-3-en-2-yl]-N-hydroxyurea |
| 8 | 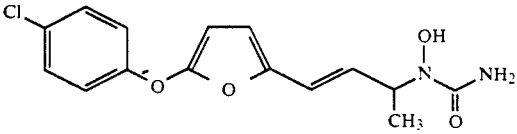<br>E-N-[4-(5-(4-chlorophenoxy)-2-furanyl)but-3-en-2-yl]-N-hydroxyurea |
| 9 | 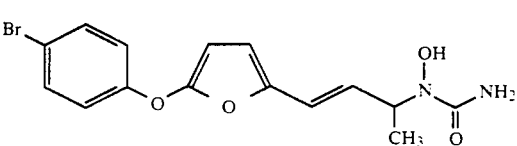<br>E-N-[4-(5-(4-bromophenoxy)-2-furanyl)but-3-en-2-yl]-N-hydroxyurea |
| 10 | 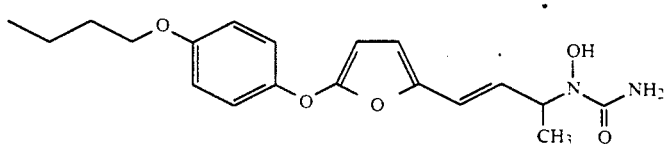<br>E-N-[4-(5-(4-n-butoxyphenoxy)-2-furanyl)but-3-en-2-yl]-N-hydroxyurea |
| 11 | 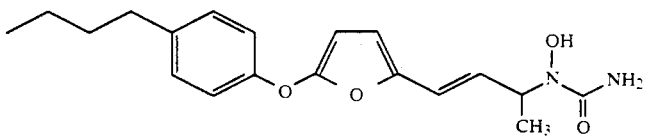<br>E-N-[4-(5-(4-n-butylphenoxy)-2-furanyl)but-3-en-2-yl]-N-hydroxyurea |
| 12 | 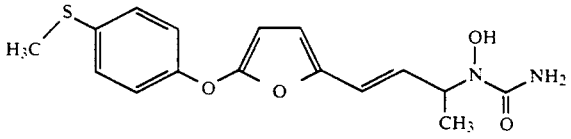<br>E-N-[4-(5-(4-thiomethylphenoxy)-2-furanyl)but-3-en-2-yl]-N-hydroxyurea |
| 13 | 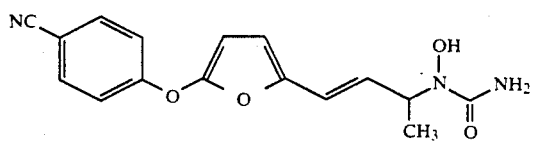<br>E-N-[4-(5-(4-cyanophenoxy)-2-furanyl)but-3-en-2-yl]-N-hydroxyurea |
| 14 | 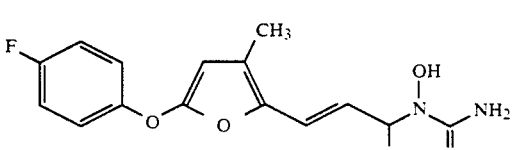<br>E-N-[4-(5-(4-fluorophenoxy)-3-methyl-2-furanyl)but-3-en-2-yl]-N-hydroxyurea |

TABLE 3-continued

| Example | Product |
|---|---|
| 15 | 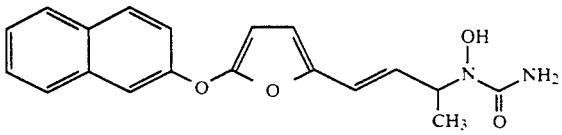 E-N-[4-(5-(2-naphthoxy)-2-furanyl)but-3-en-2-yl]-N-hydroxyurea |
| 16 | 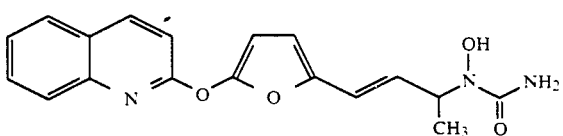 E-N-[4-(5-quinolyloxy-2-furanyl)but-3-en-2-yl]-N-hydroxyurea |
| 17 | 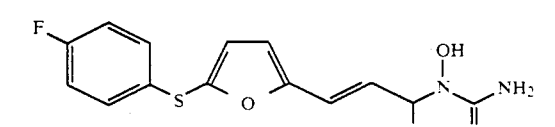 E-N-[4-(5-(4-fluorothiophenoxy)-2-furanyl)but-3-en-2-yl]-N-hydroxyurea |
| 18 | 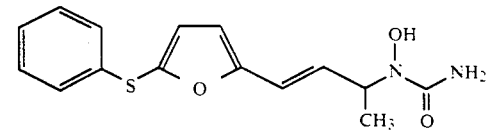 E-N-[4-(5-(4-thiophenoxy)-2-furanyl)but-3-en-2-yl]-N-hydroxyurea |
| 19 | 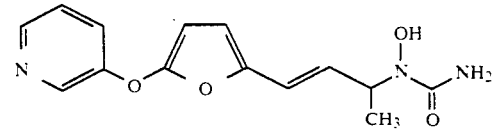 E-N-4-(5-(3-pyridnyloxy)-2-furanyl)but-3-en-2-yl]-N-hydroxyurea |
| 20 | 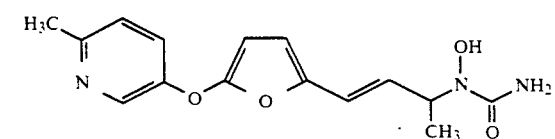 E-N-4-(5-(4-methyl-3-pyridnyloxy)-2-furanyl)but-3-en-2-yl]-N-hydroxyurea |
| 21 |  E-N-4-(5-(5-chloro-3-pyridnyloxy)-2-furanyl)but-3-en-2-yl-1-methyl-2-propenyl]-N-hydroxyurea |

TABLE 3-continued

| Example | Product |
|---|---|
| 22 | 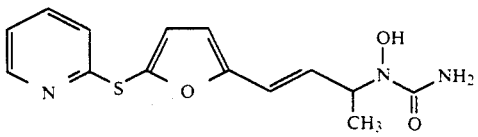<br>E-N-[4-(5-(2-mercaptopyridinyl)-2-furanyl)but-3-en-2-yl]-N-hydroxyurea |

The compounds represented in Table 4 can be prepared by treatment of the appropriately substituted hydroxylamine, prepared as in Example 1, steps a–c with 2.5 to 3.0 equivalents of acetyl chloride and triethylamine in tetrahydrofuran. The resulting N,O-diacyl hydroxylamine is selectively cleaved with lithium hydroxide in aqueous isopropyl alcohol or ammonia in methanol to yield the desired N-hydroxyacetamide.

TABLE 4

| Example | Product |
|---|---|
| 23 | 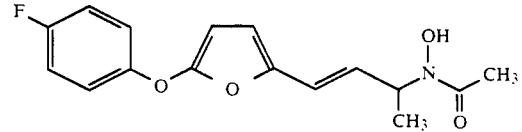<br>E-N-[4-(5-(4-fluorophenoxy)-2-furanyl)but-3-en-2-yl]-N-hydroxxacetamide |
| 24 | 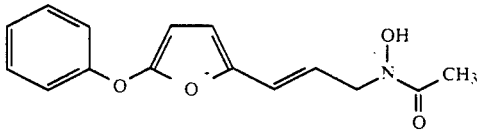<br>E-N-[3-(5-phenoxy-2-furanyl)prop-2-enyl]-N-hydroxyacetamide |
| 25 | 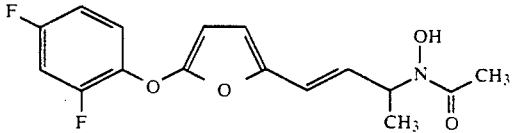<br>E-N-[4-(5-(2,4-difluorophenoxy)-2-furanyl)but-3-en-2-yl]-N-hydroxyacetamide |
| 26 | 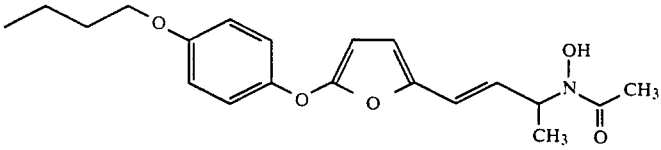<br>E-N-[4-(5-(4-n-butoxyphenoxy)-2-furanyl)but-3-en-2-yl]-N-hydroxyacetamide |
| 27 | 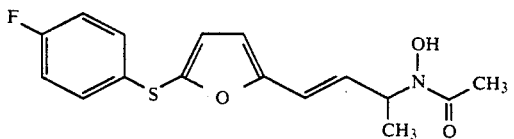<br>E-N-[4-(5-(4-fluorothiophenoxy)-2-furanyl)but-3-en-2-yl]-N-hydroxyacetamide |

TABLE 4-continued

| Example | Product |
|---|---|
| 28 | 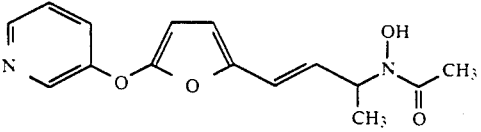<br>E-N-4-(5-(3-pyridinyloxy)-2-furanyl)but-3-en-2-yl]-N-hydroxyacetamide |

We claim:

1. A compound having the structure

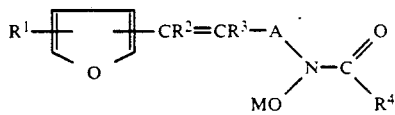   I or a pharmaceutically acceptable salt thereof wherein
A is a valence bond or is a straight or branched divalent alkylene group of from one to twelve carbon atoms;
M is selected from the group consisting of hydrogen, a pharmaceutically acceptable cation, and a pharmaceutically acceptable metabolically cleavable group;
$R^1$ is selected from the group consisting of
  phenoxy, optionally substituted with
    alkyl of from one to six carbon atoms,
    haloalkyl of from one to six carbon atoms,
    alkoxy of from one to six carbon atoms,
    hydroxy or
    halogen;
  phenyl-thio, optionally substituted with
    alkyl of from one to six carbon atoms,
    haloalkyl of from one to six carbon atoms,
    alkoxy of from one to six carbon atoms,
    hydroxy or
    halogen;
  2-,3-, or 4-pyridyloxy, optionally substituted with
    alkyl of from one to six carbon atoms,
    haloalkyl of from one to six carbon atoms,
    alkoxy of from one to six carbon atoms,
    hydroxy or
    halogen;
  2-,3-, or 4-pyridylmethoxy, optionally substituted with
    alkyl of from one to six carbon atoms,
    haloalkyl of from one to six carbon atoms,
    alkoxy of from one to six carbon atoms,
    hydroxy or
    halogen;
  1, or 2-naphthyloxy, optionally substituted with
    alkyl of from one to six carbon atoms,
    haloalkyl of from one to six carbon atoms,
    alkoxy of from one to six carbon atoms,
    hydroxy or
    halogen;
  2-,4-,5-, or 8-quinolyloxy, optionally substituted with
    alkyl of from one to six carbon atoms,
    haloalkyl of from one to six carbon atoms,
    alkoxy of from one to six carbon atoms,
    hydroxy or
    halogen; and
  2-,4-,5-, or 8-quinolylmethoxy, optionally substituted with
    alkyl of from one to six carbon atoms,
    haloalkyl of from one to six carbon atoms,
    alkoxy of from one to six carbon atoms,
    hydroxy or
    halogen;
$R^2$ and $R^3$ are independently selected from the group consisting of
  hydrogen,
  alkyl of from one to twelve carbon atoms,
  halogen, and
  trifluoroalkyl;
$R^4$ is selected from the group consisting of
  hydrogen,
  alkyl of from one to twelve carbon atoms,
  cycloalkyl of from three to eight carbon atoms, and
  —$NR^5R^6$ where
    $R^5$ is selected from the group consisting of
      hydrogen,
      alkyl of from one to six carbon atoms,
      hydroxyalkyl of from one to six carbon atoms, and
      alkoxyalkyl in which the alkoxy portion and the alkyl portion each contain, independently, from one to six carbon atoms, and
    $R^6$ is selected from the group consisting of
      hydrogen,
      alkyl of from one to six carbon atoms,
      hydroxyalkyl of from one to six carbon atoms,
      alkoxyalkyl in which the alkoxy portion and the alkyl portion each contain, independently, from one to six carbon atoms,
      alkanoyl of from two to eight carbon atoms,
      carbocyclic aryl, and
      (carbocyclic aryl)alkyl in which the alkyl portion contains from one to six carbon atoms.

2. A compound as defined by claim 1 or pharmaceutically acceptable salt thereof wherein $R^4$ is selected from alkyl of from one to twelve carbon atoms and cycloalkyl of from three to eight carbon atoms.

3. A compound as defined by claim 1 wherein $R^4$ is —$NR^5R^6$ where $R^5$ and $R^6$ are as defined therein.

4. A compound as defined by claim 3 having the structure

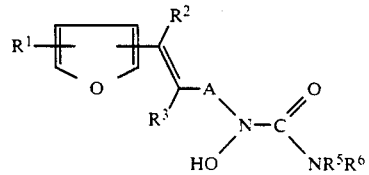

wherein A, $R^1$, $R^2$, $R^3$, $R^4$, $R^5$, and $R^6$ are as defined therein.

5. The compound having the name E-N-[4-(5-(4-fluorophenoxy)-2-furanyl)but-3-en-2-yl]-N-hydroxyurea or a pharmaceutically acceptable salt thereof.

6. A compound, or pharmaceutically acceptable salt thereof, selected from the group consisting of E-N-[3-(5-phenoxy-2-furanyl)-2-propen-1-yl]-N-hydroxyurea;

Z-N-[4-(5-(4-fluorophenoxy)-2-furanyl)-2-fluorobut-3-en-2-yl]-N-hydroxyurea;

E-N-[4-(5-phenoxy-2-furanyl)but-3-en-2-yl]-N-hydroxyurea;

E-N-[4-(5-(2-fluorophenoxy)-2-furanyl)but-3-en-2-yl]-N-hydroxyurea;

E-N-[4-(5-(2,4-difluorophenoxy)-2-furanyl)but-3-en-2-yl]-N-hydroxyurea;

E-N-[4-(5-(2-methyl-4-fluorophenoxy)-2-furanyl)but-3-en-2-yl]-N-hydroxyurea;

E-N-[4-(5-(4-chlorophenoxy)-2-furanyl)but-3-en-2-yl]-N-hydroxyurea;

E-N-[4-(5-(4-bromophenoxy)-2-furanyl)but-3-en-2-yl]-N-hydroxyurea;

E-N-[4-(5-(4-n-butoxyphenoxy)-2-furanyl)but-3-en-2-yl]-N-hydroxyurea;

E-N-[4-(5-(4-n-butylphenoxy)-2-furanyl)but-3-en-2-yl]-N-hydroxyurea;

E-N-[4-(5-(4-thiomethylphenoxy)-2-furanyl)but-3-en-2-yl]-N-hydroxyurea;

E-N-[4-(5-(4-cyanophenoxy)-2-furanyl)but-3-en-2-yl]-N-hydroxyurea;

E-N-[4-(5-(4-fluorophenoxy)-3-methyl-2-furanyl)but-3-en-2-yl]-N-hydroxyurea;

E-N-[4-(5-(2-naphthoxy)-2-furanyl)but-3-en-2-yl]-N-hydroxyurea;

E-N-[4-(5-quinolyloxy-2-furanyl)but-3-en-2-yl]-N-hydroxyurea;

E-N-[4-(5-(4-fluorothiophenoxy)-2-furanyl)but-3-en-2-yl]-N-hydroxyurea;

E-N-[4-(5-(4-thiophenoxy)-2-furanyl)but-3-en-2-yl]-N-hydroxyurea;

E-N-[4-(5-(3-pyridnyloxy)but-3-ene-2-yl]-N-hydroxyurea;

E-N-[4-(5-(6-methyl-3-pyridnyloxy)-2-furanyl)but-3-en-2-yl]-N-hydroxyurea;

E-N-[4-(5-(5-chloro-3-pyridnyloxy)-2-furanyl)but-3-en-2-yl]-N-hydroxyurea;

E-N-[4-(5-(2-mercaptopyridinyl)-2-furanyl)but-3-en-2-yl]-N-hydroxyurea;

E-N-[4-(5-(4-fluorophenoxy)-2-furanyl)but-3-en-2-yl]-N-hydroxyacetamide;

E-N-[3-(5-phenoxy-2-furanyl)-2-propenyl]-N-hydroxyacetamide;

E-N-[4-(5-(2,4-difluorophenoxy)-2-furanyl)but-3-en-2-yl]-N-hydroxyacetamide;

E-N-[4-(5-(4-n-butoxyphenoxy)-2-furanyl)but-3-en-2-yl]-N-hydroxyacetamide;

E-N-[4-(5-(4-fluorothiophenoxy)-2-furanyl)but-3-en-2-yl]-N-hydroxyacetamide; and E-N-4-(5-(3-pyridyloxy)-2-furanyl)but-3-en-2-yl]-N-hydroxyacetamide.

7. A pharmaceutical composition for inhibiting the biosynthesis of leukotrienes comprising a therapeutically effective amount of a compound as defined by claim 1 in combination with a pharmaceutically acceptable carrier.

8. A method of inhibiting the biosynthesis of leukotrienes comprising administering to a mammal in need of such treatment a therapeutically effective amount of a compound of claim 1.

* * * * *